United States Patent
Gunji

(10) Patent No.: US 9,995,673 B2
(45) Date of Patent: Jun. 12, 2018

(54) FLOW CELL

(71) Applicant: SHIMADZU CORPORATION, Kyoto-shi, Kyoto (JP)

(72) Inventor: Masahide Gunji, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 212 days.

(21) Appl. No.: 14/990,926

(22) Filed: Jan. 8, 2016

(65) Prior Publication Data

US 2016/0282317 A1    Sep. 29, 2016

(30) Foreign Application Priority Data

Mar. 25, 2015  (JP) ................. 2015-062166

(51) Int. Cl.
*G01N 21/03* (2006.01)
*G01N 21/05* (2006.01)

(52) U.S. Cl.
CPC ......... *G01N 21/05* (2013.01); *G01N 21/0317* (2013.01)

(58) Field of Classification Search
CPC ............................ G01N 21/05; G01N 21/0317
USPC .................................................. 356/432–440
See application file for complete search history.

(56) References Cited

U.S. PATENT DOCUMENTS 4,886,356 A * 12/1989 Paradis .................. G01N 21/05
                                                              356/246

FOREIGN PATENT DOCUMENTS

JP         2014-174099 A       9/2014

* cited by examiner

*Primary Examiner* — Hina F Ayub
*Assistant Examiner* — Amanda Merlino
(74) *Attorney, Agent, or Firm* — Sughrue Mion, PLLC

(57) ABSTRACT

A flow cell including a flow cell bod having a flow path formed therein; an optically transmissive member disposed at a part wherein light from the light source is incident into, or emitted from, the flow path; a shock absorbing member that is disposed between the optically transmissive member and the cell body; an elastic member, made from a metal material, for pressing the optically transmissive member toward the cell body side; and a fastening tool, attached to the cell body, for positioning the elastic member.

6 Claims, 3 Drawing Sheets

FLOW CELL

TECHNICAL FIELD

The present invention relates to a flow cell.

BACKGROUND ART

Light absorption detecting devices used in the spectrophotometers are known as one type of detecting device used in liquid chromatography. This type of light absorption detecting device is provided with a flow cell for detecting sequentially test sample components that are separated in a column (referencing, for example, Patent Citation 1).

FIG. 6 is a schematic cross-sectional diagram for explaining a conventional flow cell. To function as a flow cell 101, it is necessary to maintain the seal so that there will be no leakage between the cell body 103 and the lens 107 (or a window plate) when the mobile phase flows through the flow path 105 within the cell body 103. In a conventional flow cell 101, the seal is maintained through pressing a fluid-contacting-side gasket 111 and the lens 107 against the cell body 103 through tightening of a lens holding screw 109.

Moreover, in order to prevent breakage of the lens 107, the lens holding screw 109 is pressed into the lens 107 side through an air-side gasket 113. The materials for the fluid-contacting-side gasket 111 and the air-side gasket 113 use, for example, a resin such as PFA (a copolymer of tetrafluoroethylene and perfluoroalkyl vinyl ether) or PCTFE perfluorotrifluoro ethylene), or the like.

PRIOR ART DOCUMENT

Patent Document

[Patent Document 1] Japanese Unexamined Patent Application Publication 2014-174099

SUMMARY OF THE INVENTION

Problem Solved by the Present Invention

In the prior art, if immediately following tightening of the lens holding screw, then the lens is pressed against the cell body with an adequately strong force to maintain the seal between the lens and the cell body. However, as time passes, the fluid-contacting-side gasket and the air-side gasket deform, which relaxes the force with which the lens is pressed against the cell body. Because of this, there is a problem in that, as time passes after the assembly of the flow cell, the ability of the flow cell to withstand pressure diminishes.

The object of the present invention is to reduce degradation in the ability of the flow cell to withstand pressure.

Means for Solving the Problem

The flow cell of the embodiment according to the present invention comprises: a cell body having a flow path formed therein; an optically transmissive member disposed at a part within the flow path wherein light from a light source is incident or emitted; a sealing member disposed between the optically transmissive member and the cell body; an elastic member, made from a metal material, for pressing the optically transmissive member in the direction of the cell body; and a fastening tool that is attached to the cell body for positioning the elastic member.

Effects of the Invention

The flow cell the according to an embodiment according to the present invention can reduce degradation in the ability of the flow cell to withstand pressure.

DETAILED DESCRIPTION OF THE EXEMPLARY EMBODIMENTS

Figure 1:
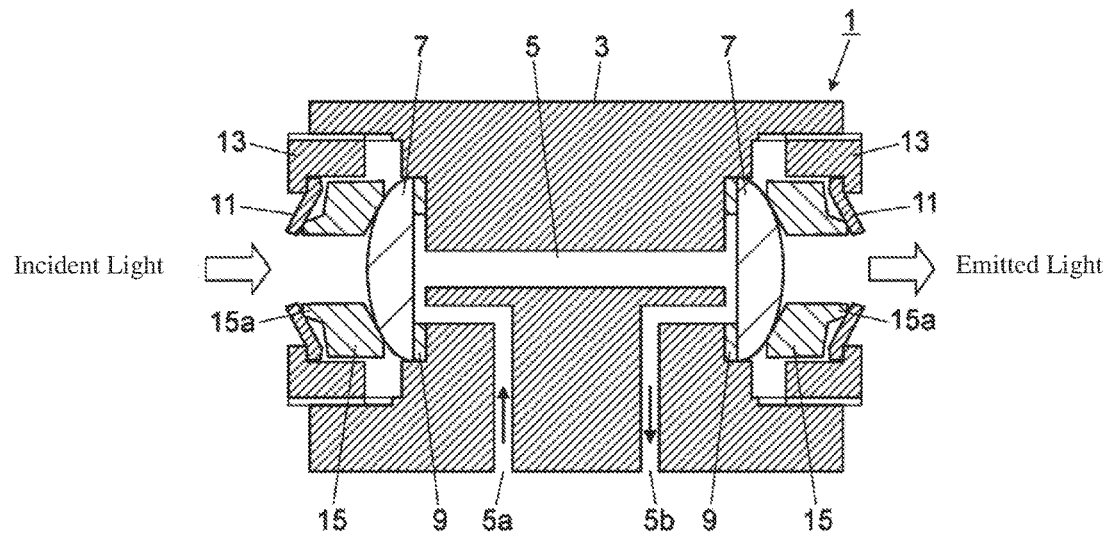
FIG. 1 is a schematic structural diagram for explaining an embodiment of a flow cell.

In a flow cell of an embodiment according to the present invention, the optically transparent member is, for example, a lens or a window plate. However, the optically transparent member is not limited to a lens or a window plate, but may be any member insofar as it is a member through which light from the light source can be incident or emitted.

Moreover, in a flow cell according to an embodiment according to the present invention, the fastening tool is, for example, a fastening screw that has a hole at the light path for the light, described above. However, there is no limitation to the fastening tool being the aforementioned fastening screw. The fastening tool may be anything that has a function that is able to secure the position of an elastic member. For example, it may be a plate-shaped member, having a hole at the light path of the light, secured to the cell body by screws.

Moreover, in the flow cell according to the embodiment according to the present invention, the elastic member has, for example, the shape of a disk spring. In the embodiment of the present invention, the "shape of a disk spring" refers to not just a truncated round conical shape with an opening in the center, but also to a flat round disk-shape with an opening in the center, including so-called flat washer shapes.

Furthermore, in the flow cell according to the present embodiment of the present invention, the fastening tool may be, for example, a fastening screw, and the elastic member that has the disk spring shape may be integrated as a single unit with the fastening screw, for example. Doing so makes it possible to reduce the number of parts in the flow cell when compared to the case wherein the elastic member having the disk spring shape and the securing screw are separate pieces, and enables a reduction in the cost for assembling the flow cell.

Moreover, in the flow cell of the embodiment of the present invention, the elastic member may be, for example, a compression spring.

Note that in the flow cell of the embodiment of the present invention, the elastic member is not limited to having a disk spring shape or to being a compression spring. Insofar as the elastic member is made from a metal material and can press the optically transparent member toward the cell body side, the shape and method of operation are arbitrary. For example, the elastic member may be a leaf spring, a spring washer, a disk-shaped washer with teeth, a corrugated washer, or the like.

Moreover, in the flow cell of the embodiment according to the present invention, a shock absorbing material made from resin may be disposed between the optically transparent member and the elastic member, where the elastic member can press the optically transparent member toward the cell body side through the shock absorbing member. Through this, the elastic member made out of the metal material can be prevented from contacting the optically transparent member directly, which could damage the optically transparent member.

FIG. 1 is a schematic structural diagram for explaining one embodiment of a flow cell. The flow cell 1 comprises a cell body 3. The cell body 3 is formed from, for example, a metal material, and here is formed out of stainless steel. A flow path 5 is formed within the cell body 3. A mobile phase that includes a test sample component that has been separated in the column of the liquid chromatograph is introduced into the flow path 5 from a mobile phase inlet 5a. The mobile phase that has been introduced into the flow path 5 is expelled from a mobile phase outlet 5b. Moreover, light from a light source is directed into the flow path 5. For example, a portion of the flow path 5 is formed in parallel to the light path of the light that is directed into the flow cell.

In the flow cell 1, lenses 7 and 7 are disposed in a part wherein light from the light source is incident into, or emitted from, the flow path 5. A lens 7 is, for example, a focusing lens, and here is a flat-convex lens. The light that is incident into the flow cell 1 enters into the flow path 5 through one of the lenses 7, and is emitted to the outside of the flow cell 1 through the other lens 7.

The fluid-contacting-side gasket 9 (a sealing member) is disposed between the lens 7 and the cell body 3. The elastic member 11 is provided in order to press the lens 7 toward the cell body 3 side. A fastening screw 13 (fastening tool) is attached to the cell body 3 in order to position the elastic member 11. The air-side gasket 15 (a shock absorbing member) is provided between the lens 7 and the elastic member 11.

The fluid-contacting-side gasket 9, the elastic member 11, and the air-side gasket 15 each have, for example, disk shapes with holes in the middle. For example, the elastic member 11 has a flat disk-shape (disk spring shape) when no load is applied. The air-side gasket 15 is provided with a protruding portion 15a at a part that contacts the elastic member 11. The fastening screw 13 is a male screw that has a hole at the light path for the light that is incident into the flow cell 1, for example.

The liquid-contacting-side gasket 9 and the air-side gasket 15 are formed from, for example, a fluorine resin such as PFA, PCTFE, or the like. The elastic member 11 and the fastening screw 13 are formed from a metal material such as stainless steel, or the like.

The elastic member 11 is deformed through tightening of the fastening screw 13, and the seal is maintained through the air-side gasket 11, the lens 7, and the liquid-contacting-side gasket 9 being pressed toward the cell body 3 side by the force of restitution of the elastic member 11.

In the flow cell 1 according to the present embodiment, a disk-shaped (flat washer-shaped) elastic member 11 is disposed between the fastening screw 13 and the air-side gasket 15. As illustrated in FIG. 1, the elastic member 11 is deformed through tightening of the fastening screw 13, and the lens 7 is pressed towards the cell body 3 side.

In the flow cell 1 according to the present embodiment, even if the fluid-contacting-side gasket 9 and the air-side gasket 15 deform as time elapses, if the amount of deformation of the elastic member 11 is sufficient, then the force pressing the lens 7 will be maintained. Consequently, there will be no degradation of the sealing performance of the lens 7. In this way, it is possible to reduce the degradation of the pressure durability performance of the flow cell 1.

Figure 2:
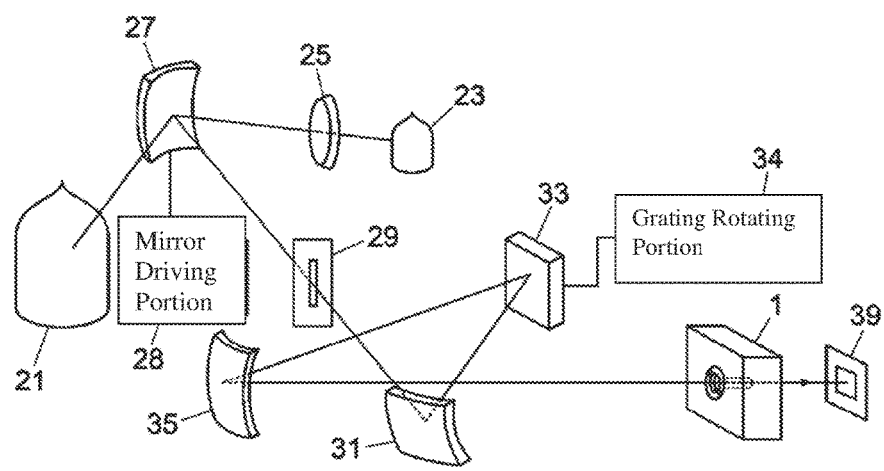
FIG. 2 is a schematic structural diagram for explaining one example of an optics system for a detector to which the flow cell according to the embodiment is applied.

FIG. 2 is a schematic structural diagram for explaining one example of an optics system in a detecting device to which the flow cell in the present embodiment is applied.

A D2 lamp 21 and a tungsten lamp 23, for example, are provided as light sources. A filter 25 is provided in the light path of the tungsten lamp 23. A mirror 27 is provided in the joint light path of the D2 lamp 21 and the tungsten lamp 23. A mirror driving portion 28 is provided for selecting a light source by rotating the mirror 27. A slit 29 is provided on the light path of the light that is reflected by the mirror 27. The slit 29 has a long rectangular opening portion, to cause the light reflected by the mirror 27 to be light of the slit-shape. A mirror 31 is provided in the light path of the light from the slit 29.

A grating 33 for diffracting the light that is incident from the light source is provided in the light path of the light reflected from the mirror 31. A grating rotating portion 34 for rotating the grating 33 to direct diffracted light to the mirror 35 is provided. A mirror 35 is provided for directing, to the flow cell 1, the light diffracted by the grating 33. A photodetector 39 for detecting, using a photodetecting element, light that passes through the flow cell 1 is provided on the side of the flow cell 1 that is opposite from the side illuminated with light.

The light from the D2 lamp 21 and from the tungsten lamp 23 is directed toward the mirror 27. The light from the tungsten lamp 23 is directed to the mirror 27 through the filter 25. The mirror 27 is rotated by the mirror driving portion 28 to select a light source, and the reflected light from that light source is directed to the slit 29, to become slit-shaped light. This light is reflected by the mirror 31 to pass through the grating 33, to be diffracted. The grating 33 is rotated by the grating driving portion 34, and the diffracted light is focused on the flow cell 1 by the mirror 35.

The slit-shaped light that has passed through the slit 29 is collimated by the mirror 31, the grating 33, and the mirror 35. This light is caused to pass through the light path 5 (referencing FIG. 1) of the flow cell 1. The light that has passed through the light path 5 is detected by the photodetector 39, and is converted into an amount of optical absorption, to calculate the amount of light absorbed by the test sample component, to detect the target component.

Note that the optics system for the detecting device to which the flow cell is applied in the embodiment according to the present invention is not limited to the optics system illustrated in FIG. 2.

Figure 3:
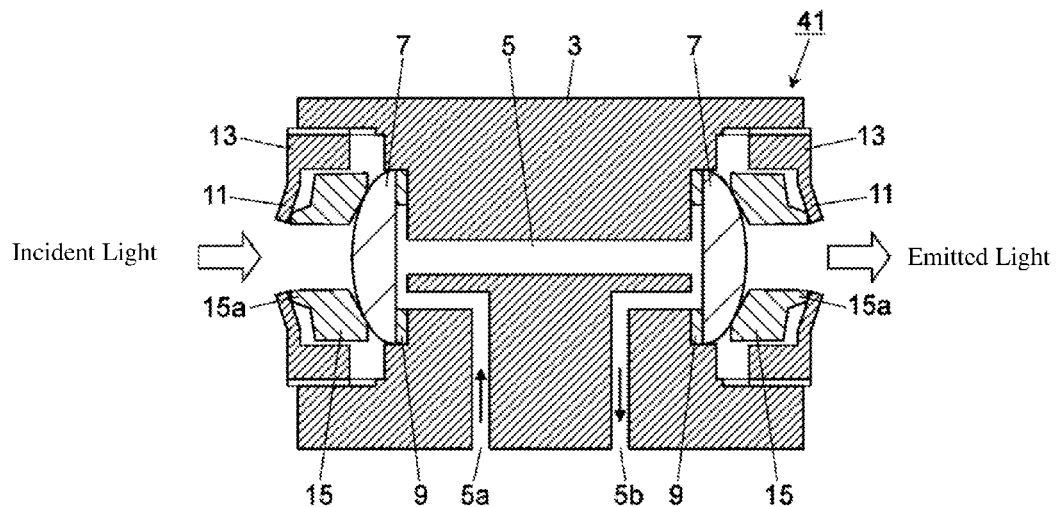
FIG. 3 is a schematic structural diagram for explaining another embodiment of a flow cell.

FIG. 3 is a schematic structural diagram for explaining another embodiment of a flow cell. In FIG. 3, those parts that achieve identical functions to those in FIG. 1 are assigned identical codes, and detailed explanations of those parts are omitted.

In the flow cell 41 according to the present embodiment, the elastic member 11 is integrated with the fastening screw 13. Because of this, it is possible to reduce in the flow cell 41 the number of parts and compared to the flow cell 1 that is illustrated in FIG. 1. As a result, the flow cell 41 is able to reduce the assembly cost when compared to the flow cell 1 that is illustrated in FIG. 1.

Figure 4:
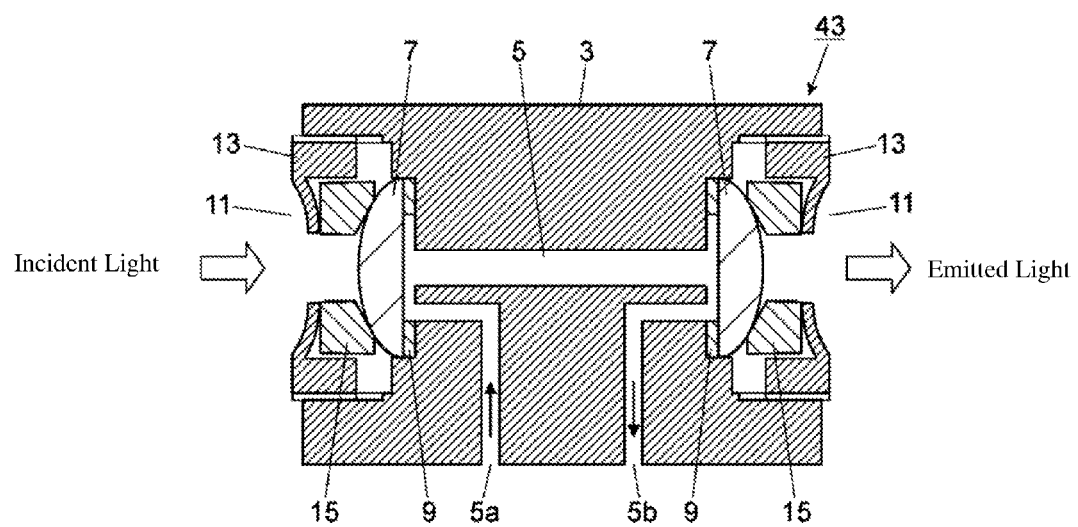
FIG. 4 is a schematic structural diagram for explaining yet another embodiment of a flow cell.

FIG. 4 is a schematic structural diagram for explaining yet another embodiment of a flow cell. In FIG. 4, those parts that achieve identical functions to those in FIG. 1 are assigned identical codes, and detailed explanations of those parts are omitted.

In the flow cell 43 according to the present embodiment, the elastic member 11 is integrated with the fastening screw 13. Additionally, the elastic member 11 has a truncated conical shape (a disk spring shape), with the top face side disposed on the lens 7 side. The elastic member 11 produces a spring effect through the deformation of the truncated round conical shape so that the height thereof is reduced. Moreover, in the flow cell 43, the air-side gasket 15 is not provided with the protruding portion 15a (referencing FIG. 1).

The elastic member 11 having the truncated round conical shape makes it possible to transmit, to the lens 7, the force of restitution of the elastic member 11, even without forming a protruding portion 15a on the air-side gasket 15. This makes it possible to simplify the shape of the air-side gasket 15, enabling a reduction in the manufacturing cost of the flow cell through, for example, using a commercially available gasket.

Figure 5:
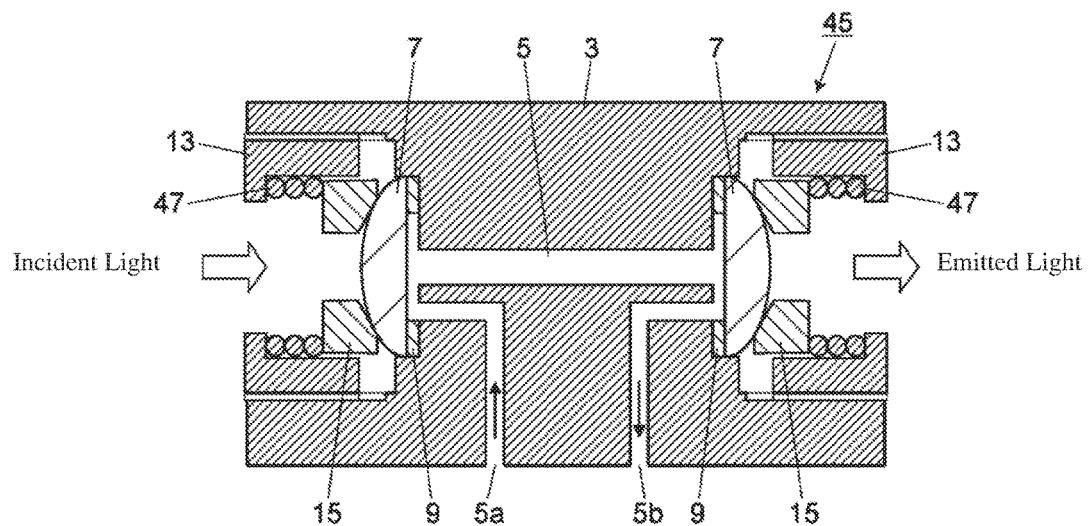
FIG. 5 is a schematic structural diagram for explaining yet another embodiment of a flow cell.
Figure 6:
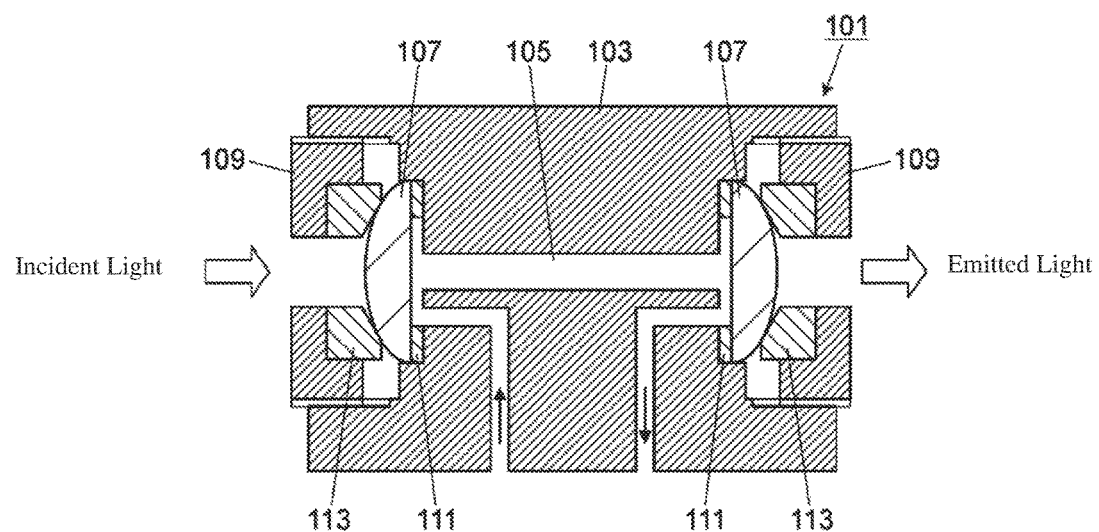
FIG. 6 is a schematic cross-sectional diagram for explaining a conventional flow cell.

FIG. 5 is a schematic structural diagram for explaining yet another embodiment of a flow cell. In FIG. 5, those parts that achieve identical functions to those in FIG. 1 are assigned identical codes, and detailed explanations of those parts are omitted.

In the flow cell 45 according to the present embodiment, when compared to the flow cell 1 illustrated in FIG. 1, a coil-shaped compression spring 47 is provided instead of the elastic member 11. The compression spring 47 is formed from a metal material, formed from, for example, stainless steel wire.

The compression spring 47 is compressed through tightening of the fastening screw 13, and the air-side gasket 15, the lens 7, and the fluid-contacting-side gasket 9 are pressed towards the cell body 3 side by the force of restitution of the compression spring 47. Note that in the flow cell 45, the protruding portion 15a (referencing FIG. 1) is not provided on the air-side gasket 15.

The flow cell 45 according to the present embodiment enables a simplification in the shape of the securing screw, thus enabling a reduction in the manufacturing cost of the flow cell. Moreover, if a commercially available compression spring, for example, can be used as the compression spring 47, this enables a reduction in the manufacturing cost of the flow cell.

While embodiments of the present invention were explained below, the structures, placements, materials, sizes, and the like, of the various members in the embodiments are examples, and the present invention is not limited thereto, but rather can be modified in a variety of ways within the scope of the present invention, as set forth in the patent claims.

For example, in a flow cell of an embodiment according to the present invention, a window plate may be used instead of a lens. Note that in a flow cell of an embodiment according to the present invention, the optically transparent member is a member through which light from the light source can be incident or emitted.

Moreover, in a flow cell of an embodiment according to the present invention, the shock-absorbing member 15 is not limited to being a so-called "gasket." In the flow cell of the embodiment according to the present invention, the shock-absorbing member made from resin that is disposed between the elastic member and the optically transmissive member has no particular limitation in terms of the material, shape, size, or the like, insofar as it is able to prevent contact between the elastic member, which is made from a metal material, and the optically transmissive member, to thereby prevent damage to the optically transmissive member. Moreover, in the flow cell of an embodiment according to the present invention, this shock-absorbing member need not necessarily be provided.

EXPLANATION OF CODES 1, 41, 43, 45: Flow Cells
3: Cell Body
5: Flow Path
7: Lens (Optically Transmissive Member)
9: Fluid-Contacting-Side Gasket (Sealing Member)
11: Elastic Member
13: Fastening Screw (Fastening Tool)
15: Air-Side Gasket (Sock-Absorbing Member)
43: Compression Spring (Elastic Member)

What is claimed:
1. A flow cell comprising:
a cell body having a flow path formed therein;
an optically transmissive member disposed at a part within the flow path wherein light from a light source is incident or emitted;
a sealing member disposed between the optically transmissive member and the cell body;
an elastic metal member having a disk spring shape, for pressing the optically transmissive member in the direction of the cell body; and
a fastening tool that is attached to the cell body for positioning the elastic metal member,
wherein the fastening tool is a fastening screw, and the elastic metal member is integrated with the fastening screw.
2. A flow cell as set forth in claim 1, wherein:
the optically transmissive member is a lens or a window plate.
3. A flow cell as set forth in claim 1, wherein:
the fastening tool is a fastening screw having a hole at the light path of the light.
4. A flow cell as set forth in claim 1, wherein:
the elastic metal member has a truncated conical disk spring shape.
5. A flow cell as set forth in claim 1, wherein:
the elastic metal member is a compression spring.
6. A flow cell as set forth in claim 1, wherein:
a shock absorbing gasket made from resin is disposed between the optically transmissive member and the elastic metal member; and
the elastic metal member presses the optically transmissive member toward the cell body side through the shock absorbing gasket.

* * * * *